United States Patent
Kimura et al.

(10) Patent No.: US 9,329,172 B2
(45) Date of Patent: May 3, 2016

(54) METHOD FOR ANALYZING BLOOD CELLS AND BLOOD CELL ANALYZER

(71) Applicant: Sysmex Corporation, Kobe-shi Hyogo (JP)

(72) Inventors: Konobu Kimura, Kobe (JP); Kinya Uchihashi, Kobe (JP)

(73) Assignee: SYSMEX CORPORATION, Kobe-Shi (JP)

( * ) Notice: Subject to any disclaimer, the term of this patent is extended or adjusted under 35 U.S.C. 154(b) by 0 days.

(21) Appl. No.: 14/084,022

(22) Filed: Nov. 19, 2013

(65) Prior Publication Data

US 2014/0147837 A1    May 29, 2014

(30) Foreign Application Priority Data

Nov. 26, 2012 (JP) ................................ 2012-258004

(51) Int. Cl.
| | | |
|---|---|---|
| *C12M 1/34* | (2006.01) | |
| *G06K 9/00* | (2006.01) | |
| *G01N 33/50* | (2006.01) | |
| *G01N 15/14* | (2006.01) | |
| *G01N 15/00* | (2006.01) | |
| *G01N 15/10* | (2006.01) | |

(52) U.S. Cl.
CPC ........ *G01N 33/5094* (2013.01); *G01N 15/1459* (2013.01); *G01N 2015/008* (2013.01); *G01N 2015/1006* (2013.01); *G01N 2015/1477* (2013.01)

(58) Field of Classification Search
CPC .................................. C12M 1/34; G06K 9/00
USPC ........................................ 435/288.7; 382/134
See application file for complete search history.

(56) References Cited

U.S. PATENT DOCUMENTS

| 2007/0020721 A1* | 1/2007 | Yoshida et al. ................ 435/34 |
| 2011/0027788 A1 | 2/2011 | Zhao et al. |
| 2012/0282601 A1 | 11/2012 | Abe et al. |

FOREIGN PATENT DOCUMENTS

| CN | 101046439 A | 10/2007 |
| CN | 101086473 A | 12/2007 |
| CN | 101403739 A | 4/2009 |
| CN | 101726611 A | 6/2010 |
| CN | 101852733 A | 10/2010 |
| CN | 101988082 A | 3/2011 |
| CN | 102472738 A | 5/2012 |
| CN | 102768179 A | 11/2012 |
| JP | 2006-091024 A | 4/2006 |
| WO | WO 2012/147451 A1 | 11/2012 |

OTHER PUBLICATIONS

Inoue, H. Overview of Automated Hemotology Analyzer XE-2100; Sysmex Journal International, vol. 9, No. 1 (1999) pp. 58-64.*
Anonymous. Chapter 7 Functional Description; Sysmex XE-2100 Operator's Manual (2007) pp. 7-1 to 7-37. downloaded from www.cmmc.org/cmmclab/IFU/XE-2100.pdf on Oct. 24, 2014.*
Anonymous. Dynamic Analysis SYSMEX XE 2100 (2015), downloaded from http://www.analisisinstruments.com/index.php?route=product/product_id=115 on May 1, 2015.*
Davey et al. Multivariate Data Analysis Methods for the Interpretation of Microbial Flow Cytometric Data; Advanced Biochemical Engineering and Biotechnology, vol. 124 (2010) pp. 183-209.*
Briggs et al. Improved Flagging Rates on the Sysmex XE-5000 Compared With the XE-2100 Reduce the Number of Manual Film Reviews and Increase Laboratory Productivity; American Journal of Clinical Pathology, vol. 136 (2011) pp. 309-316.*

* cited by examiner

*Primary Examiner* — Kagnew H Gebreyesus
*Assistant Examiner* — Paul Martin
(74) *Attorney, Agent, or Firm* — Brinks Gilson & Lione

(57) ABSTRACT

A method for analyzing blood cells includes: preparing a measurement specimen for classifying white blood cells, by mixing a sample with a reagent in order to hemolyze red blood cells contained in the sample and to fluorescently stain nucleic acid in white blood cells contained in the sample; detecting, by flowing the prepared measurement specimen in a flow cell, fluorescence emitted from each blood cell in the measurement specimen and two types of scattered light at respective different angles, and obtaining a fluorescence signal and two types of scattered light signals; and classifying the white blood cells into at least four groups and detecting neoplastic lymphocytes, by performing analysis using at least three types of parameters based on the obtained fluorescence signal and two types of scattered light signals.

18 Claims, 10 Drawing Sheets

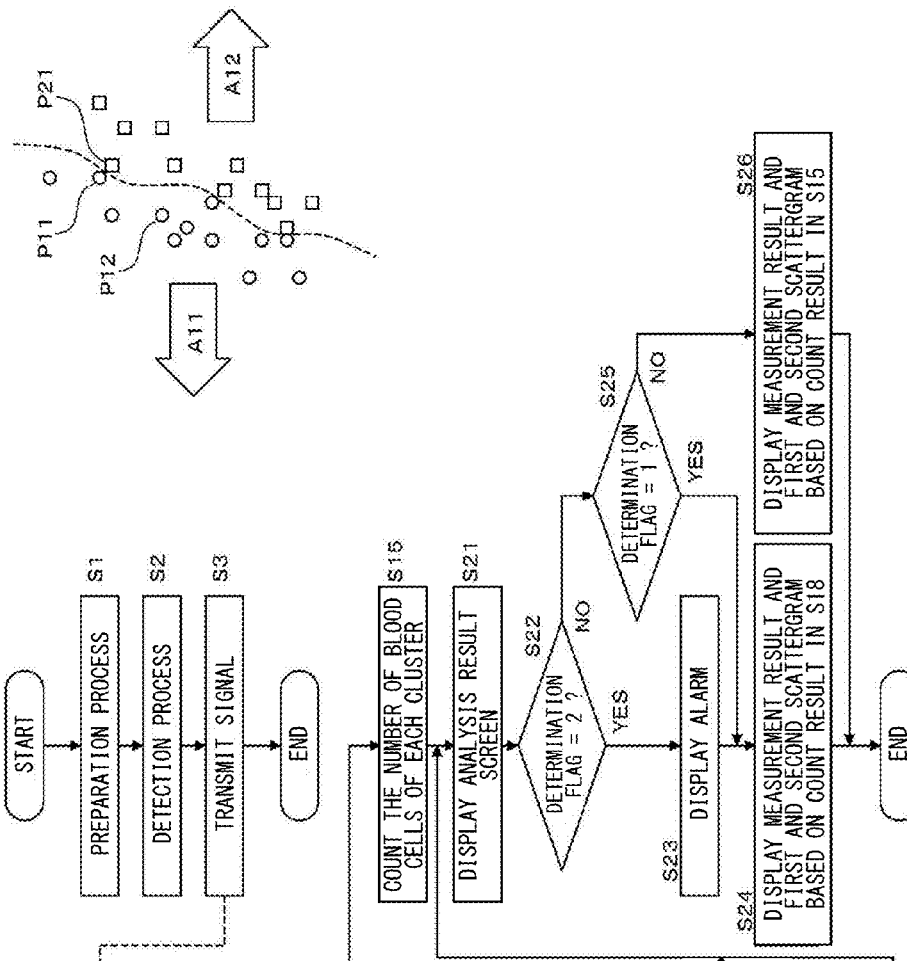
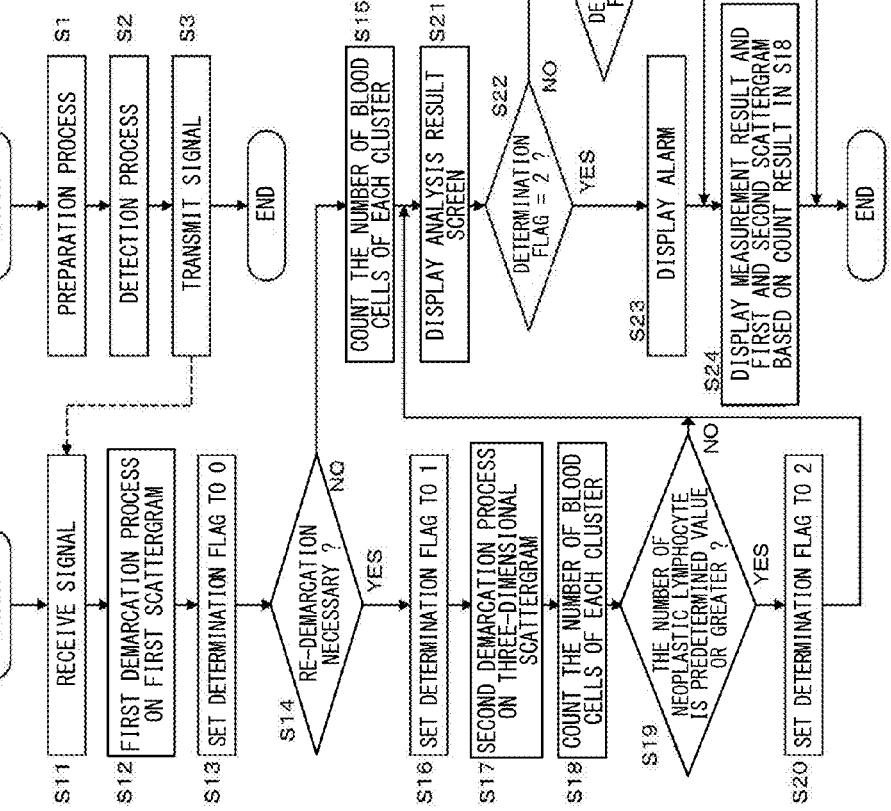
FIG. 6A
FIG. 6B

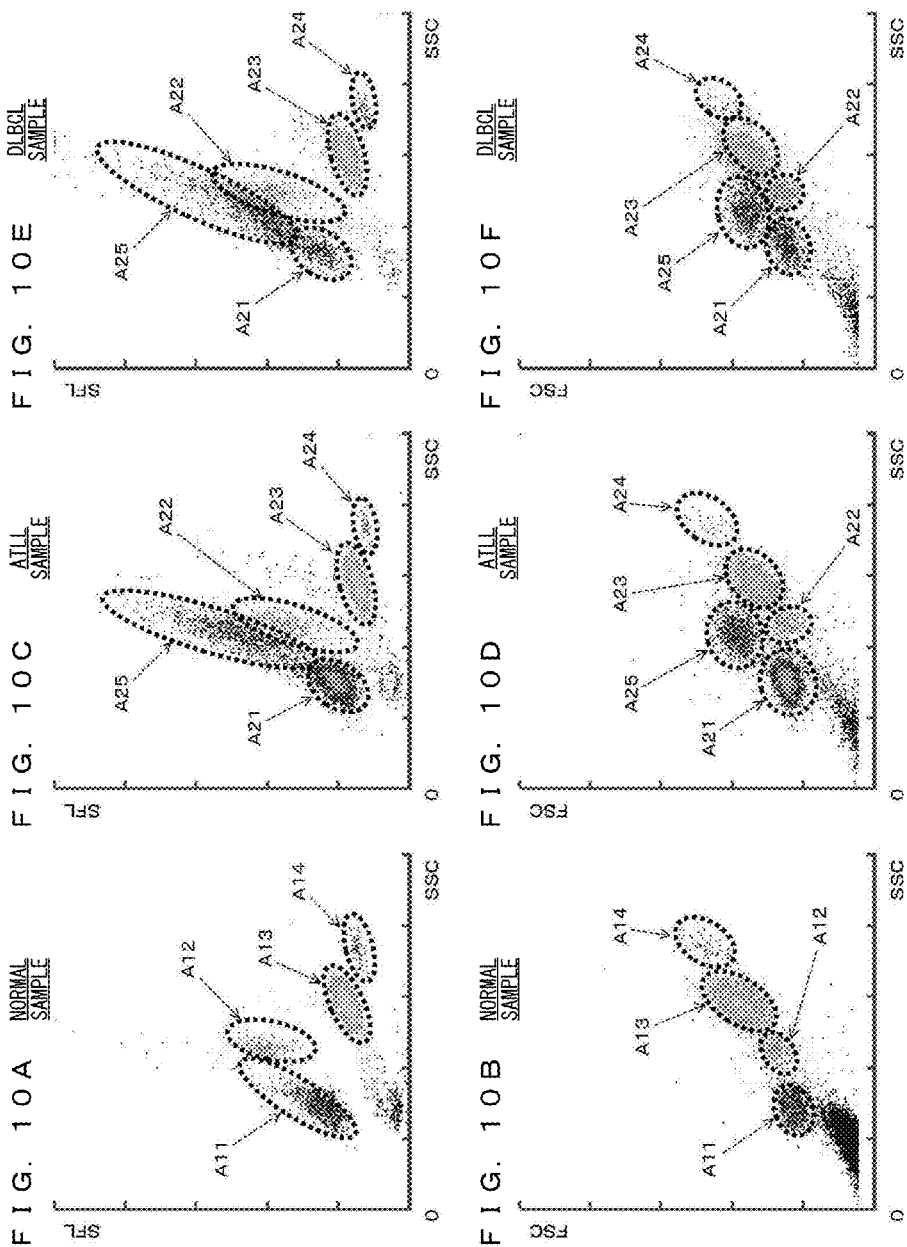

METHOD FOR ANALYZING BLOOD CELLS AND BLOOD CELL ANALYZER

RELATED APPLICATIONS

This application claims priority under 35 U.S.C. §119 to Japanese Patent Application No. 2012-258004 filed on Nov. 26, 2012, the entire content of which is hereby incorporated by reference.

FIELD OF THE INVENTION

The present invention relates to a method for analyzing blood cells and a blood cell analyzer for each classifying and counting white blood cells in a sample.

BACKGROUND OF THE INVENTION

Typically, normal white blood cells are classified into five types: lymphocyte, monocyte, basophil, eosinophil, and neutrophil. In normal peripheral blood, these types of blood cells exist at certain ratios. However, if a subject has a disease, there may be cases where the number of blood cells of a specific type increases or decreases. Therefore, in the field of clinical laboratory tests, information highly useful for disease diagnosis can be obtained by classifying and counting white blood cells.

On the other hand, in peripheral blood of a patient having a disease, cells that do not exist in normal peripheral blood appear. For example, in the case of diseases such as chronic lymphocytic leukemia, malignant lymphoma, and the like, neoplastic mature lymphocytes appear in peripheral blood. In the case of acute leukemia, "blast cells (myeloblasts, lymphoblasts)" which are immature white blood cells appear in peripheral blood. Further, in the case of viral infection, drug allergy, and the like, "atypical lymphocytes", which are lymphocytes activated by being primed appear in peripheral blood. Therefore, in order to accurately classify white blood cells, it is necessary to detect these abnormal cells separately from other normal white blood cells.

Japanese Laid-Open Patent Publication No. 2006/91024 describes: preparing a measurement specimen by mixing a blood specimen with a hemolytic agent and a dye compound; measuring scattered light and fluorescence occurring from each blood cell in the measurement specimen by use of a flow cytometer; classifying white blood cells into five groups based on measurement data; and detecting abnormal cells such as atypical lymphocytes, myeloblasts, and the like separately from normal white blood cells based on the measurement data.

SUMMARY OF THE INVENTION

The scope of the present invention is defined solely by the appended claims, and is not affected to any degree by the statements within this summary.

The technology of Japanese Laid-Open Patent Publication No. 2006/91024 cannot detect neoplastic mature lymphocytes as abnormal cells. Therefore, it is desired to improve accuracy of classifying white blood cells by detecting neoplastic mature lymphocytes.

In view of the above problem, an object of the present invention is to provide a method for analyzing blood cells, a blood cell analyzer, and a program which each allow easy detection of neoplastic lymphocytes and improvement of accuracy of classifying and counting normal white blood cells.

A first aspect of the present invention refers to a method for analyzing blood cells. The method for analyzing blood cells according to this aspect includes: preparing a measurement specimen for classifying white blood cells, by mixing a sample with a reagent in order to hemolyze red blood cells contained in the sample and to fluorescently stain nucleic acid in white blood cells contained in the sample; detecting, by flowing the measurement specimen in a flow cell, fluorescence emitted from each blood cell in the measurement specimen and two types of scattered light at respective different angles, and obtaining a fluorescence signal and two types of scattered light signals; and classifying the white blood cells into at least four groups and detecting neoplastic lymphocytes, by performing analysis using at least three types of parameters based on the fluorescence signal and the two types of scattered light signals.

In the method for analyzing blood cells according to the present aspect, neoplastic lymphocytes are detected, separately from non-neoplastic other blood cells. Therefore, accuracy of classifying normal white blood cells can be increased, and diagnosis of disease based on the classification can be performed more appropriately. Further, since neoplastic lymphocytes are detected, separately from other blood cells, information useful for diagnosis of diseases such as chronic lymphocytic leukemia, malignant lymphoma, and the like can be provided to the user.

A second aspect of the present invention relates to a method for analyzing blood cells. The method for analyzing blood cells according to this aspect includes: preparing a measurement specimen by mixing a sample with a reagent; detecting, by flowing the measurement specimen in a flow cell, fluorescence emitted from each blood cell in the measurement specimen and two types of scattered light at respective different angles, and obtaining a fluorescence signal and two types of scattered light signals; detecting neoplastic lymphocytes, by performing analysis using at least three types of parameters based on the fluorescence signal and the two types of scattered light signals; and displaying information regarding the detected neoplastic lymphocytes on a display unit.

In the method for analyzing blood cells according to the present aspect, neoplastic lymphocytes are detected and information regarding the detected neoplastic lymphocytes is displayed on the display unit. Therefore, information useful for diagnosis of diseases such as chronic lymphocytic leukemia, malignant lymphoma, and the like can be provided to the user.

A third aspect of the present invention relates to a blood cell analyzer. The blood cell analyzer according to this aspect includes: a specimen preparation section configured to prepare a measurement specimen for classifying white blood cells, by mixing a sample with a reagent in order to hemolyze red blood cells contained in the sample and to fluorescently stain nucleic acid in white blood cells contained in the sample; a detection section configured to detect fluorescence emitted from each blood cell in the measurement specimen and two types of scattered light at respective different angles, and configured to output a fluorescence signal and two types of scattered light signals; and an information processing unit configured to classify the white blood cells into at least four groups and configured to detect neoplastic lymphocytes, by performing analysis using at least three types of parameters regarding the fluorescence and the two types of scattered light based on the fluorescence signal and the two types of scattered light signals.

In the blood cell analyzer according to the present aspect, neoplastic lymphocytes are detected, separately from non-neoplastic other blood cells. Therefore, accuracy of classifying normal white blood cells can be increased, and diagnosis of disease based on the classification can be performed more appropriately. Further, since neoplastic lymphocytes are detected, separately from other blood cells, information useful for diagnosis of diseases such as chronic lymphocytic leukemia, malignant lymphoma, and the like can be provided to the user.

As described above, according to the present invention, a method for analyzing blood cells and a blood cell analyzer that each allow easy detection of neoplastic lymphocytes and improvement of accuracy of classifying and counting normal white blood cells can be provided.

The effects and the significance of the present invention will be further clarified by the description of the embodiment below. However, the embodiment below is merely an example for implementing the present invention. The present invention is not limited by the embodiment below in any way.

BRIEF DESCRIPTION OF THE DRAWINGS

FIGS. 6A and 6B show flow charts of processes performed by a measurement unit and an information processing unit according to an embodiment and shows an example of a part where two clusters are close to each other on a first scattergram;

FIG. 8 shows a configuration of an analysis result screen according to an embodiment;

FIG. 9 shows a configuration of an analysis result screen according to an embodiment; and FIGS. 10A to 10F show first and second scattergrams displayed in an analysis result screen according to an embodiment.

DETAILED DESCRIPTION OF THE PREFERRED EMBODIMENTS

The preferred embodiments of the present invention will be described hereinafter with reference to the drawings.

The present embodiment is obtained by applying the present invention to a blood cell analyzer for performing tests and analysis regarding blood. Hereinafter, a blood cell analyzer according to the present embodiment will be described with reference to the drawings.

Figure 1:
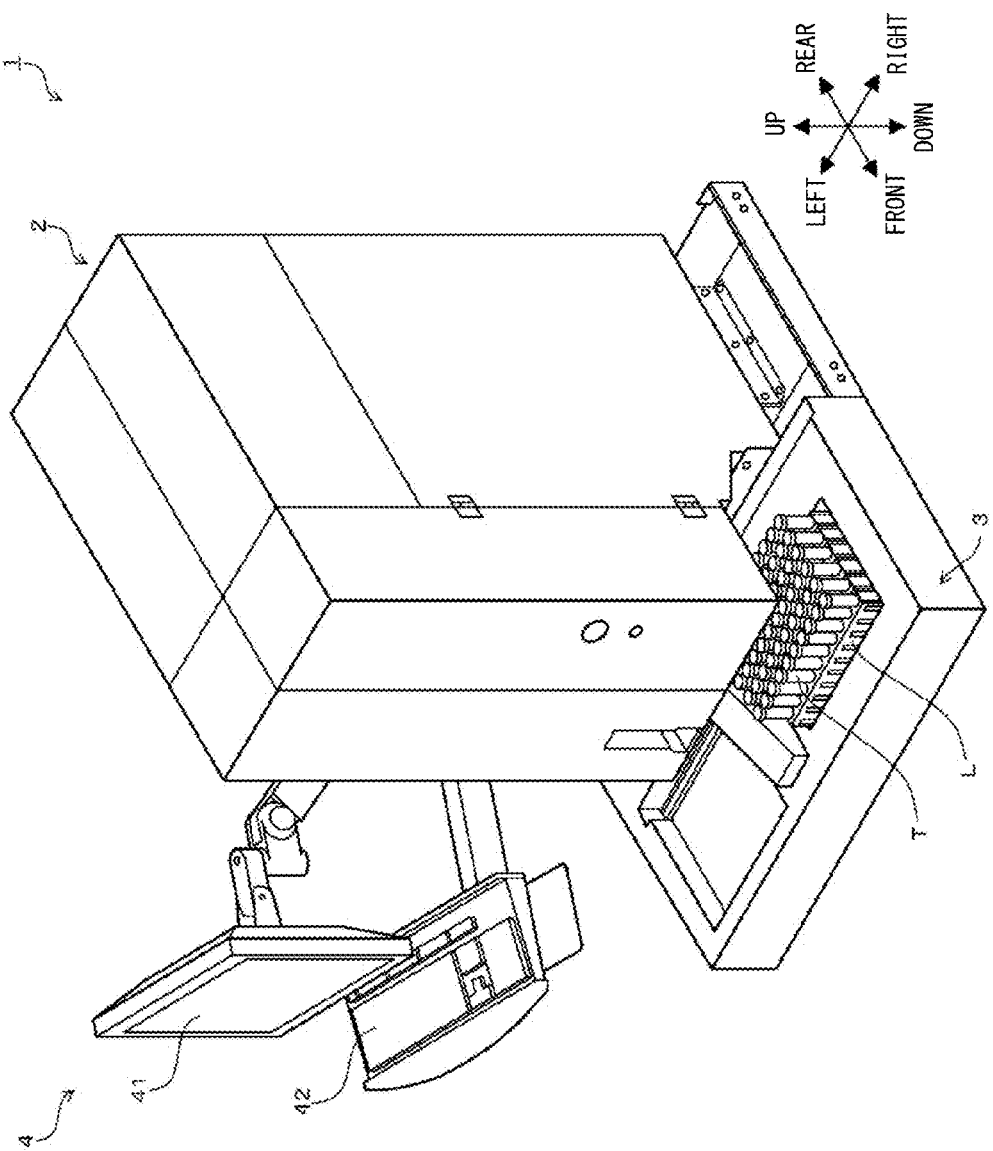
FIG. 1 is a perspective view showing an external view of a blood cell analyzer according to an embodiment.

FIG. 1 is a perspective view showing an external view of a blood cell analyzer 1 according to the present embodiment.

The blood cell analyzer 1 is a multi-item blood cell analyzer which detects white blood cells, red blood cells, platelets, and the like contained in a blood sample and which counts each type of blood cells. The blood cell analyzer 1 includes a measurement unit 2, a transporting unit 3 arranged to the front face side of the measurement unit 2, and an information processing unit 4. A blood sample being peripheral blood collected from a patient is contained in a sample container (blood collecting tube) T. A plurality of sample containers T are held in a sample rack L, and the sample rack L is transported by the transporting unit 3, whereby blood samples are supplied to the measurement unit 2.

Figure 2:
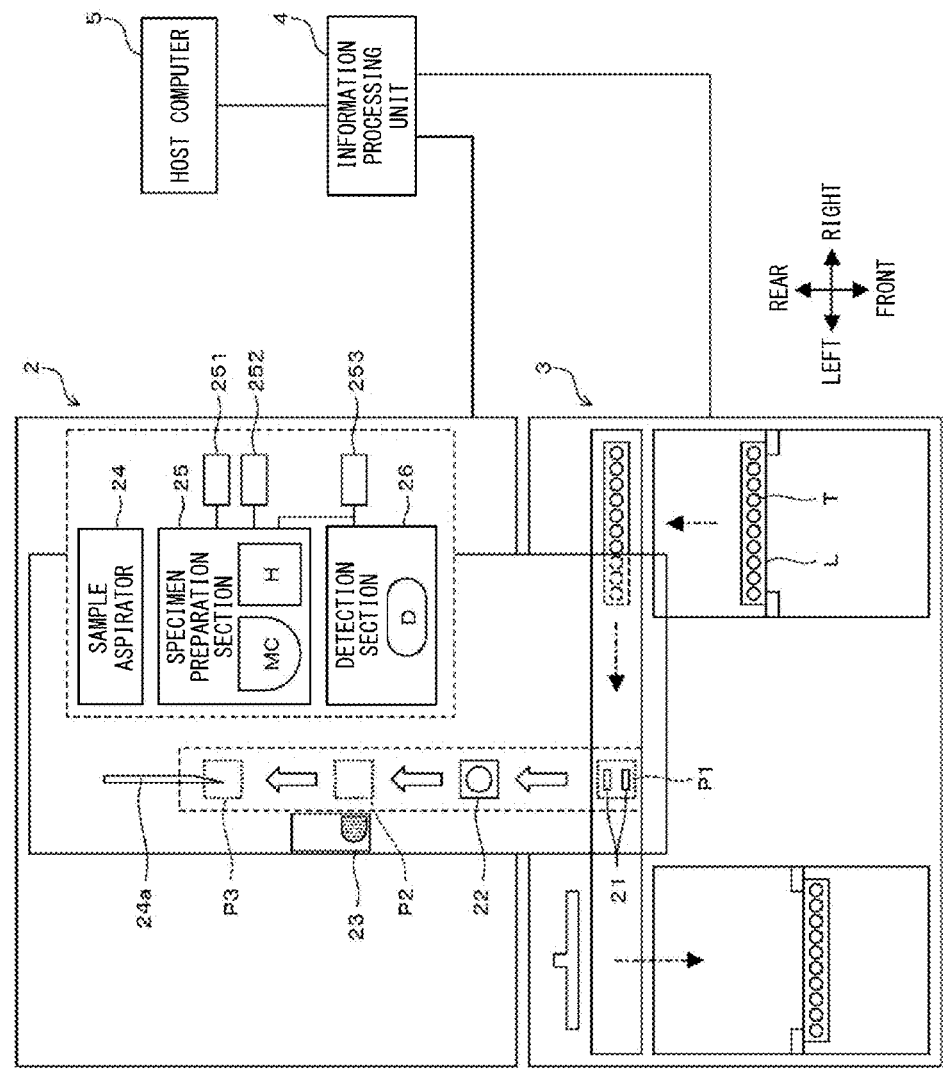
FIG. 2 is a schematic diagram showing a configuration of a measurement unit according to an embodiment.

The information processing unit 4 includes a display unit 41 and an input unit 42 and is communicably connected to the measurement unit 2, the transporting unit 3, and a host computer 5 (see FIG. 2). The information processing unit 4 controls operation of the measurement unit 2 and the transporting unit 3, performs analysis based on a result of measurement performed by the measurement unit 2, and transmits an analysis result to the host computer 5 (see FIG. 2).

FIG. 2 is a schematic diagram showing a configuration of the measurement unit 2.

The measurement unit 2 includes a hand part 21, a sample container setting part 22, a bar code unit 23, a sample aspirator 24, a specimen preparation section 25, and a detection section 26. The sample aspirator 24 includes a piercer 24a and aspirates a sample from a sample container T. The specimen preparation section 25 includes a mixing chamber MC and a heater H, and prepares a measurement specimen to be used in measurement, by mixing the sample with a reagent. The detection section 26 includes an optical detector D, and detects blood cells from the measurement specimen. Each component of the measurement unit 2 is controlled by the information processing unit 4.

A sample container T located at a position P1 by the transporting unit 3 is gripped by the hand part 21, and upwardly pulled out of the sample rack L. Then, by the hand part 21 being swung, the sample in the sample container T is stirred. The sample container T for which stirring has been completed is set, by the hand part 21, to the sample container setting part 22 located at the position P1. Then, the sample container T is transported to a position P2 by the sample container setting part 22.

When the sample container T is located at the position P2, the bar code unit 23 provided at the vicinity of the position P2 reads a sample number from a bar code label attached to the sample container T. Then, the sample container T is transported to a position P3 by the sample container setting part 22. When the sample container T is located at the position P3, a predetermined amount of the sample is aspirated from the sample container T by the sample aspirator 24 via the piercer 24a. After the aspiration of the sample has been completed, the sample container T is transported forward by the sample container setting part 22, and returned to the original holding position in the sample rack L by the hand part 21. After the piercer 24a has been transferred to a position corresponding to the mixing chamber MC, the sample aspirated via the piercer 24a is discharged by a predetermined amount into the mixing chamber MC by the sample aspirator 24.

The specimen preparation section 25 is connected, via tubes, to a reagent container 251 containing a first reagent, a reagent container 252 containing a second reagent, and a reagent container 253 containing a sheath fluid (diluent). Further, the specimen preparation section 25 is connected to a compressor (not shown), and can receive an aliquot of each of the reagents from the reagent containers 251 to 253, by use of a pressure generated by this compressor. The specimen preparation section 25 mixes the blood sample, the first reagent, and the second reagent together in the mixing chamber MC, and heats the mixture solution for a predetermined time period by means of the heater H, to prepare a measurement specimen. The measurement specimen prepared by the specimen preparation section 25 is supplied to the optical detector D of the detection section 26.

The detection section 26 is connected, via a tube, to the reagent container 253 containing the sheath fluid (diluent).

Further, the detection section 26 is connected to a compressor (not shown) and can receive an aliquot of the sheath fluid (diluent) from the reagent container 253 by use of a pressure generated by this compressor.

Figure 3:
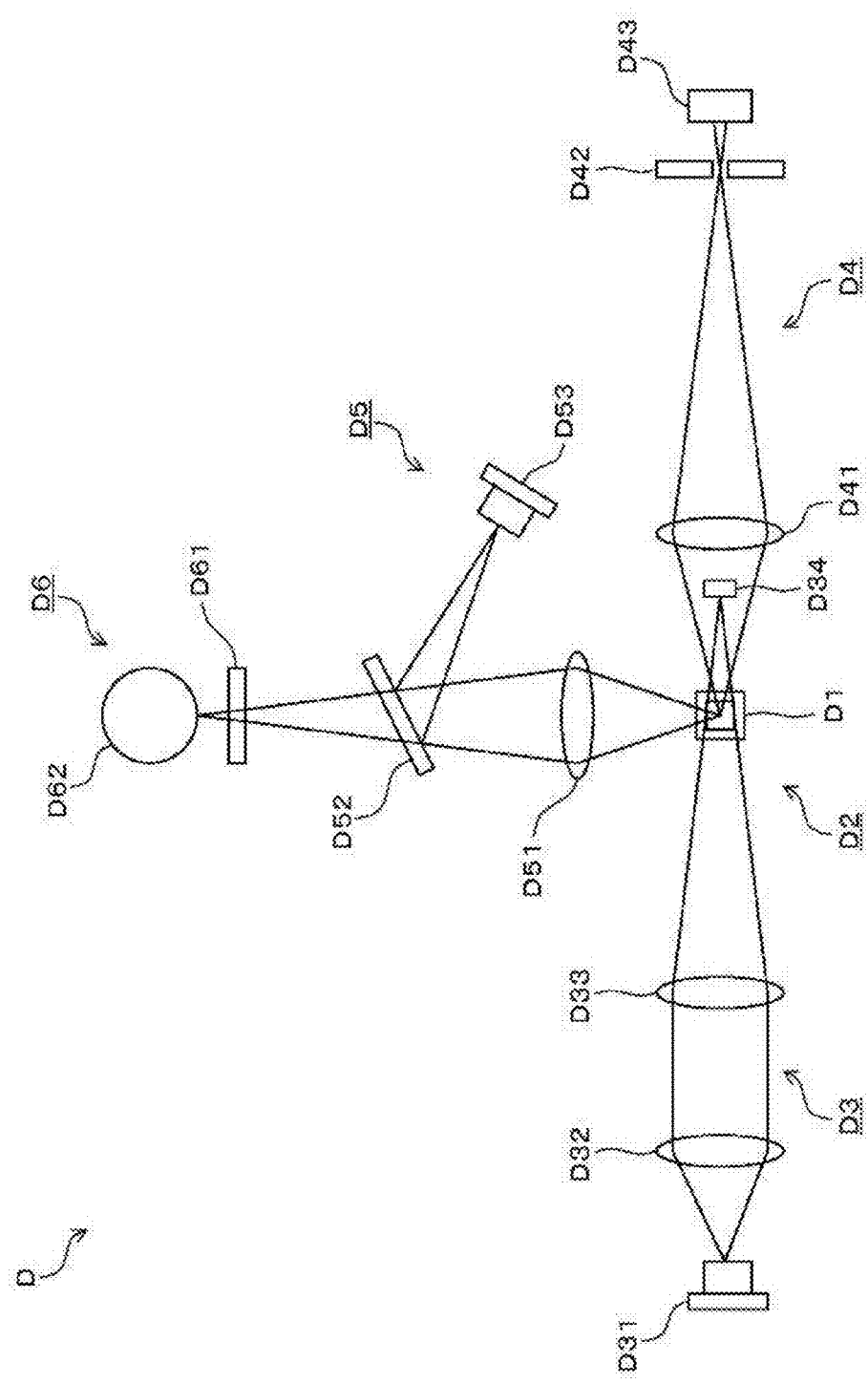
FIG. 3 is a schematic plan view showing a configuration of an optical detector according to an embodiment.

FIG. 3 is a schematic diagram showing a configuration of the optical detector D. The optical detector D includes a flow cell D1, a sheath flow system D2, a beam spot formation system D3, a forward scattered light receiving system D4, a side scattered light receiving system D5, and a fluorescence receiving system D6.

The sheath flow system D2 is configured to send, into the flow cell D1, a measurement specimen surrounded in a sheath fluid, and to generate a fluid flow in the flow cell D1. The beam spot formation system D3 is configured such that light emitted from a semiconductor laser D31 advances through a collimator lens D32 and a condenser lens D33 to irradiate the flow cell D1. Accordingly, each blood cell contained in the fluid flow passing through the flow cell D1 is irradiated with a laser beam. Further, the beam spot formation system D3 includes a beam stopper D34.

The forward scattered light receiving system D4 is configured to condense scattered light advancing forward (forward scattered light) with a forward condenser lens D41, and to receive light that has passed through a pinhole D42 with a photodiode D43. The photodiode D43 outputs a forward scattered light signal (FSC) based on a peak value of the received forward scattered light. The side scattered light receiving system D5 is configured to condense scattered light advancing sideways (side scattered light) with a side condenser lens D51, and to cause a part of the side scattered light to be reflected at a dichroic mirror D52 to be received by a photodiode D53. The photodiode D53 outputs a side scattered light signal (SSC) based on a peak value of the received side scattered light.

Light scattering is a phenomenon that occurs when the advancing direction of light is changed due to the presence of a particle such as a blood cell as an obstacle in the advancing direction of the light. By detecting this scattered light, information regarding the size and the material of the particle can be obtained. In particular, from forward scattered light, information regarding the size of a particle (blood cell) can be obtained. Further, from side scattered light, information regarding the inside of a particle can be obtained. When a blood cell particle is irradiated with a laser beam, the intensity of side scattered light is dependent on the complexity (the shape, size, and density of the nucleus and the amount of granules) inside the cell.

The fluorescence receiving system D6 is configured to allow light (fluorescence), of the side scattered light, that has transmitted through the dichroic mirror D52, to further pass through a spectrum filter D61 to be received by an avalanche photodiode D62. The avalanche photodiode D62 outputs a fluorescence signal (SFL) based on a peak value of the received fluorescence.

When a blood cell stained by a fluorescent substance is irradiated with light, the blood cell emits fluorescence having a wavelength longer than the wavelength of the light that irradiated the blood cell. The intensity of fluorescence increases if the blood cell is well stained, and by measuring this fluorescence intensity, information regarding the stained degree of the blood cell can be obtained.

With reference back to FIG. 2, the forward scattered light signal, the side scattered light signal, and the fluorescence signal, which have been obtained by the optical detector D, are transmitted to the information processing unit 4. The information processing unit 4 performs analysis based on these received signals. In this analysis, white blood cells present in the blood sample are classified into four subclasses (lymphocyte (LYMPH), monocyte (MONO), blood cell group including neutrophil (NEUT) and basophil (BASO), and eosinophil (EO)).

Although description is omitted in the present embodiment, the blood cell analyzer 1 mixes a blood sample with a predetermined reagent to prepare a measurement specimen for counting the number of white blood cells and individually detecting basophils. By measuring the measurement specimen using the optical detector D, the number of white blood cells can be obtained and classification of neutrophils and basophils can be performed.

Figure 4:
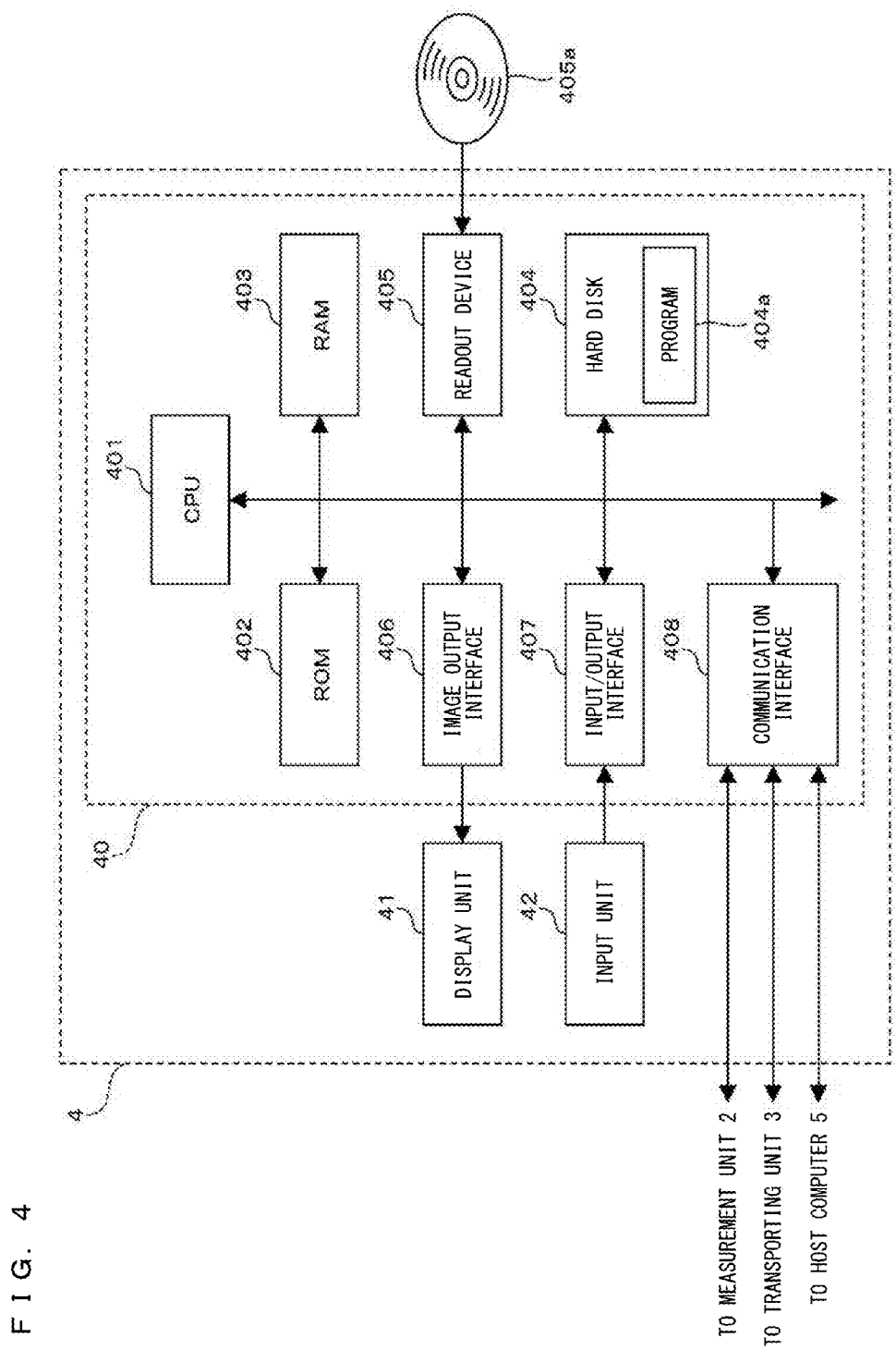
FIG. 4 shows a configuration of an information processing unit according to an embodiment.

FIG. 4 shows a configuration of the information processing unit 4.

The information processing unit 4 is implemented by a personal computer, and includes a body 40, the display unit 41, and the input unit 42. The body 40 includes a CPU 401, a ROM 402, a RAM 403, a hard disk 404, a readout device 405, an image output interface 406, an input/output interface 407, and a communication interface 408.

The CPU 401 executes computer programs stored in the ROM 402 and computer programs loaded onto the RAM 403. The RAM 403 is used for reading out computer programs stored in the ROM 402 and the hard disk 404. Further, the RAM 403 is also used as a work area for the CPU 401 when the CPU 401 executes these computer programs.

The hard disk 404 has stored therein an operating system, computer programs to be executed by the CPU 401, and data used for execution of such computer programs. Further, the hard disk 404 has stored therein a program 404a to be executed by the CPU 401 for performing processes for the information processing unit 4 shown in FIG. 6A. The readout device 405 is implemented by a CD drive, a DVD drive, or the like, and can read out computer programs and data stored in a storage medium 405a. In a case where the program 404a is stored in the storage medium 405a, the program 404a read out from the storage medium 405a by the readout device 405 is stored in the hard disk 404.

The image output interface 406 outputs an image signal corresponding to image data to the display unit 41, and the display unit 41 displays an image based on the image signal outputted from the image output interface 406. A user inputs an instruction via the input unit 42, and the input/output interface 407 receives a signal inputted via the input unit 42. The communication interface 408 is connected to the measurement unit 2, the transporting unit 3, and the host computer 5, and the CPU 401 transmits/receives instruction signals and data to/from these apparatuses via the communication interface 408.

In the specimen preparation section 25, in order to hemolyze red blood cells, and to damage cell membranes of white blood cells to an extent that a fluorescent dye can permeate therethrough to stain nucleic acid in the white blood cells, a blood sample and reagents are mixed together, whereby a measurement specimen is prepared. Specifically, the following first reagent and second reagent are mixed with a blood sample to prepare a measurement specimen.

The first reagent contains a fluorescent dye capable of staining nucleic acid and is a reagent for fluorescently staining nucleic acid in each nucleated cell contained in the blood specimen processed by the second reagent described later. By processing a blood specimen with the first reagent, blood cells containing nucleic acid, such as white blood cells, are stained.

The fluorescent dye is not limited to a particular one as long as it can stain nucleic acid, and can be selected as appropriate in accordance with the wavelength of light emitted from a light source (the semiconductor laser D31). Examples of such a fluorescent dye include propidium iodide, ethidium bromide, ethidium-acridine heterodimer, ethidium diazide, ethidium homodimer-1, ethidium homodimer-2, ethidium monoazide, trimethylenebis[[3-[[4-[[(3-methylbenzothiazole-3-ium)-2-yl]methylene]-1,4-dihydroquinoline]-1-yl]propyl]dimethylaminium].tetraiodide (TOTO-1), 4-[(3-methylbenzothiazole-2(3H)-ylidene)methyl]-1-[3-(trimethylaminio)propyl]quinolinium.diiodide (TO-PRO-1), N,N,N',N'-tetramethyl-N,N'-bis[3-[4-[3-[(3-methylbenzothiazole-3-ium)-2-yl]-2-propenylidene]-1,4-dihydroquinoline-1-yl]propyl]-1,3-propanediaminium.tetraiodide (TOTO-3), 2-[3-[[1-[3-(trimethylaminio)propyl]-1,4-dihydroquinoline]-4-ylidene]-1-propenyl]-3-methylbenzothiazole-3-ium.diiodide (TO-PRO-3), and fluorescent dyes represented by general formula (I) below. Among these examples, the fluorescent dyes represented by general formula (I) are preferable.

[Chemical formula 1]

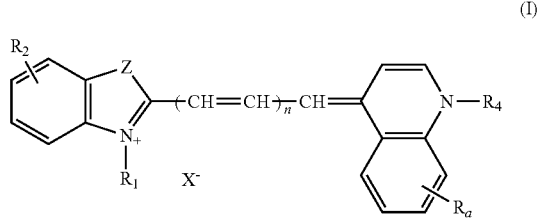

(I)

In formula (I) above, $R_1$ and $R_4$ are the same with each other or different from each other, and each are a hydrogen atom, an alkyl group, an alkyl chain having a hydroxy group, an alkyl chain having an ether group, an alkyl chain having an ester group, or a benzyl group that may have a substituent. $R_2$ and $R_3$ are the same with each other or different from each other, and each are a hydrogen atom, a hydroxyl group, a halogen, an alkyl group, an alkenyl group, an alkynyl group, an alkoxy group, an alkyl sulfonyl group, or a phenyl group. Further, Z is a sulfur atom, an oxygen atom, or a carbon atom having a methyl group, n is 0, 1, 2, or 3, and $X^-$ is an anion.

In the present embodiment, an alkyl group may be either linear or branched. Further, in formula (I) above, in a case where either one of $R_1$ and $R_4$ is an alkyl group having 6 to 18 carbon atoms, the other is preferably is an hydrogen atom or an alkyl group having fewer than 6 carbon atoms. Among alkyl groups having 6 to 18 carbon atoms, an alkyl group having 6, 8, or 10 carbon atoms is preferable.

Further, examples of the substituent of the benzyl group represented by $R_1$ and $R_4$ in formula (I) above include alkyl groups having 1 to 20 carbon atoms, alkenyl groups having 2 to 20 carbon atoms, and alkynyl groups having 2 to 20 carbon atoms. Among these, a methyl group or an ethyl group is particularly preferable.

Further, examples of the alkenyl group represented by $R_2$ and $R_3$ in formula (I) above include alkenyl groups having 2 to 20 carbon atoms. Examples of the alkoxy group represented by $R_2$ and $R_3$ include alkoxy groups having 1 to 20 carbon atoms. Among these, a methoxy group or an ethoxy group is particularly preferable.

Further, examples of the anion $X^-$ in formula (I) above include halogen ions such as $F^-$, $Cl^-$, $Br^-$, and $I^-$, and $CF_3SO_3^-$, $BF_4^-$ and the like.

Further, the fluorescent dye in the first reagent may include one, or two or more types of fluorescent dyes.

The concentration of the fluorescent dye in the first reagent may be set as appropriate in accordance with the type of the fluorescent dye, and is normally 0.01 to 100 pg/µL, and preferably 0.1 to 10 pg/µL. For example, in a case where the fluorescent dye represented by formula (I) above is used as the fluorescent dye of the first reagent, the concentration of the fluorescent dye in the first reagent is preferably 0.2 to 0.6 pg/µL, and more preferably 0.3 to 0.5 pg/µL.

The first reagent can be obtained by dissolving the fluorescent dye described above in an appropriate solvent at the concentration described above. The solvent is not limited to a particular one as long as it can dissolve the fluorescent dye described above. Examples of the solvent include water, an organic solvent, and a mixture of these. Examples of the organic solvent include alcohol, ethylene glycol, dimethyl sulfoxide (DMSO), and the like. There are cases where a fluorescent dye is not stable when preserved in an aqueous solution, and thus, the fluorescent dye is preferably dissolved in an organic solvent.

Further, as the first reagent, a commercially-available staining reagent for classifying white blood cells may be used. Examples of such a staining reagent include Stromatolyser (registered trademark)-4DS manufactured by Sysmex Corporation. Stromatolyser-4DS is a staining reagent containing a fluorescent dye represented by formula (I) above.

The second reagent contains a surfactant, i.e., a cationic surfactant and/or a nonionic surfactant, for hemolyzing red blood cells and for damaging cell membranes of white blood cells to an extent that the fluorescent dye in the first reagent can permeate therethrough. Further, the second reagent contains an aromatic organic acid at a concentration not lower than 20 mM and not higher than 50 mM. Here, with respect to the second reagent, in a case where the concentration of the aromatic organic acid is not lower than 20 mM and lower than 30 mM, pH of the second reagent is not lower than 5.5 and not higher than 6.4, and in a case where the concentration of the aromatic organic acid is not lower than 30 mM and not higher than 50 mM, pH of the second reagent is not lower than 5.5 and not higher than 7.0.

In the present embodiment, in a case where the concentration of the aromatic organic acid in the second reagent is not lower than 20 mM and lower than 30 mM, pH of the second reagent is preferably not lower than 5.5 and not higher than 6.4, and more preferably, not lower than 5.5 and not higher than 6.2. Further, in a case where the concentration of the aromatic organic acid in the second reagent is not lower than 30 mM and not higher than 50 mM, preferably not lower than 40 mM and not higher than 50 mM, pH of the second reagent is not lower than 5.5 and not higher than 7.0. More preferably, in a case where the concentration of the aromatic organic acid in the second reagent is not lower than 40 mM and not higher than 50 mM, pH of the second reagent is not lower than 5.5 and not higher than 6.2.

Further, in the present embodiment, the aromatic organic acid means an acid having at least one aromatic ring in the molecule or a salt thereof. Examples of the aromatic organic acid include aromatic carboxylic acids, aromatic sulfonic acids, and the like. In the present embodiment, phthalic acid, benzoic acid, salicylic acid, hippuric acid, p-aminobenzenesulfonic acid, benzenesulfonic acid, and salts thereof are preferably used. It should be noted that the aromatic organic acid in the second reagent may include one, or two or more types of aromatic organic acids. In a case where two or more types of aromatic organic acids are included in the second reagent, it is sufficient that the total of concentrations of these is not lower than 20 mM and not higher than 50 mM.

As the cationic surfactant, a quaternary ammonium salt type surfactant or a pyridinium salt type surfactant can be used.

Examples of the quaternary ammonium salt type surfactant include surfactants having 9 to 30 carbon atoms in total, represented by formula (II) below.

[Chemical formula 2]

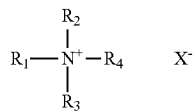
(II)

In formula (II) above, $R_1$ is an alkyl or alkenyl group having 6 to 18 carbon atoms. $R_2$ and $R_3$ are the same with each other or different from each other, and each are an alkyl or alkenyl group having 1 to 4 carbon atoms. $R_4$ is an alkyl or alkenyl group having 1 to 4 carbon atoms, or a benzyl group, and $X^-$ is a halogen atom.

In formula (II) above, $R_1$ is preferably an alkyl or alkenyl group having 6, 8, 10, 12, or 14 carbon atoms, and in particular, a linear alkyl group is preferable. More specific examples of $R_1$ include an octyl group, a decyl group, and a dodecyl group. $R_2$ and $R_3$ each are preferably a methyl group, an ethyl group, or a propyl group. $R_4$ is preferably a methyl group, an ethyl group, or a propyl group.

Examples of the pyridinium salt type surfactant include surfactants represented by formula (III) below.

[Chemical formula 3]

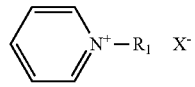
(III)

In formula (III) above, $R_1$ is an alkyl or alkenyl group having 6 to 18 carbon atoms, and $X^-$ is a halogen atom.

In formula (III) above, $R_1$ is preferably an alkyl or alkenyl group having 6, 8, 10, 12, or 14 carbon atoms, and in particular, a linear alkyl group is preferable. More specific examples of $R_1$ include an octyl group, a decyl group and a dodecyl group.

The concentration of the cationic surfactant in the second reagent can be adjusted as appropriate in accordance with the type of the surfactant, and is normally 10 to 10000 ppm, and preferably 100 to 1000 ppm.

As the nonionic surfactant, a polyoxyethylene-based nonionic surfactant represented by formula (VI) below is preferable.

$$R_1-R_2-(CH_2CH_2O)_n-H \quad (VI)$$

In formula (VI) above, $R_1$ is an alkyl, alkenyl, or alkynyl group having 8 to 25 carbon atoms, $R_2$ is an oxygen atom, —COO—, or

[Chemical formula 4]

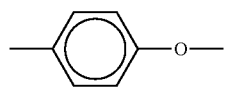

and n is an integer of 10 to 50.

Specific examples of the nonionic surfactant above include polyoxyethylene alkyl ether, polyoxyethylene sterol, polyoxyethylene castor oil, polyoxyethylene sorbitol fatty acid ester, polyoxyethylene alkyl amine, polyoxyethylene polyoxypropylene alkyl ether, and the like.

The concentration of the nonionic surfactant in the second reagent is normally 10 to 100000 ppm, preferably 100 to 10000 ppm, and more preferably 1000 to 5000 ppm.

The second reagent may include a buffer agent in order to maintain constant pH. Examples of such a buffer agent include citrates, HEPES, phosphates, and the like. It should be noted that the aromatic organic acids described above may exhibit buffer action. In a case where such an aromatic organic acid is used, addition of a buffer agent to the second reagent is optional.

The osmotic pressure of the second reagent is not limited to a particular one, but is preferably 20 to 150 mOsm/kg from the view point of efficiently hemolyzing red blood cells.

The second reagent can be obtained by dissolving the surfactant and the aromatic organic acid or a salt thereof described above, optionally with the buffer agent described above, in an appropriate solvent at the concentration of the aromatic organic acid described above, and by adjusting pH using NaOH, HCl, or the like. The solvent is not limited to a particular one as long as it can dissolve the above components, and examples of the solvent include water, an organic solvent and a mixture thereof. Examples of the organic solvent include alcohol, methanol, ethylene glycol, DMSO, and the like.

As the second reagent, a commercially available hemolyzing reagent for classifying white blood cells may be used. Examples of such a hemolyzing reagent include Stromatolyser-4DL manufactured by Sysmex Corporation. Stromatolyser-4DL is a hemolyzing reagent containing the cationic surfactant and the nonionic surfactant described above.

By the second reagent composed as described above, red blood cells are hemolyzed and cell membranes of white blood cells are damaged to an extent that the fluorescent dye in the first reagent passes therethrough. Further, by the first reagent composed as described above, white blood cells whose cell membranes have been damaged by the second reagent are stained. Accordingly, the optical detector D can perform detection of the four subclasses of white blood cell.

Procedures of classifying white blood cells in a blood sample obtained from a normal sample, the procedures being performed in analysis by the information processing unit 4, will be described.

Figure 5B:
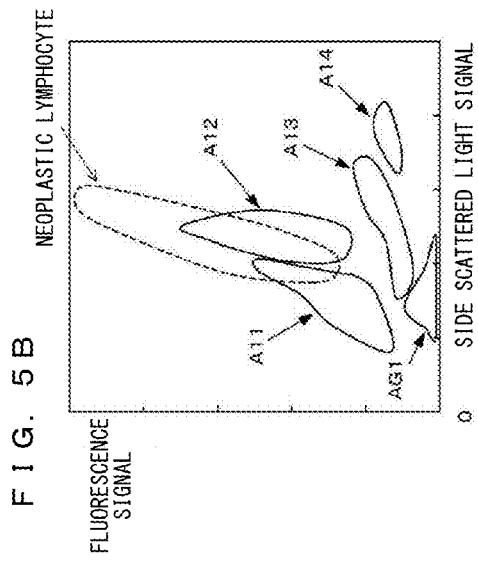
FIGS. 5A to 5C show first scattergrams and clusters on the first scattergrams according to an embodiment.
Figure 5A:

In the information processing unit 4, a first scattergram as shown in FIG. 5A is created first. Specifically, based on a side scattered light signal and a fluorescence signal regarding each individual blood cell, the first scattergram is created by plotting a dot corresponding to each individual blood cell onto a two-dimensional distribution chart whose horizontal axis represents side scattered light signal and whose vertical axis represents fluorescence signal. Such a two-dimensional distribution chart including fluorescence signal as an axis is conventionally used in order to detect blood cells (such as juvenile blood cells and the like) whose nucleic acid is very active.

Next, from the dots plotted on the first scattergram, dots corresponding to red blood cell ghosts being hemolyzed red blood cells and the like are excluded. Specifically, dots included in a predetermined region AG1 set in advance as shown in the schematic diagram in FIG. 5B are excluded. Subsequently, each dot on the first scattergram from which blood cells in the region AG1 have been excluded is classified into any of four clusters respectively corresponding to the four subclasses of white blood cell (a cluster A11 of lymphocytes, a cluster A12 of monocytes, a cluster A13 of the blood cell group including neutrophils and basophils, and a cluster A14 of eosinophils).

Specifically, based on the distance between a dot corresponding to each blood cell plotted on the first scattergram and the center of gravity of each cluster set in advance, the belonging degree of each blood cell to each cluster is obtained. Then, based on these belonging degrees, each blood cell is assigned to a corresponding cluster. Such a method for classifying blood cells is described in detail in Japanese Laid-Open Patent Publication No. H5-149863 (corresponding U.S. Pat. No. US5555196). All of the documents referred to herein are incorporated herein, in their entirety, by the reference.

When each blood cell is classified to any of the four clusters respectively corresponding to the four subclasses of white blood cell, dots plotted on the first scattergram shown in FIG. 5A will be separated into the clusters A11 to A14 shown in FIG. 5B.

Here, there are cases where a blood sample collected from a patient includes neoplastic lymphocytes. For example, if a patient has chronic lymphocytic leukemia, malignant lymphoma, or the like, a blood sample obtained from this patient may include neoplastic lymphocytes.

Figure 5C:
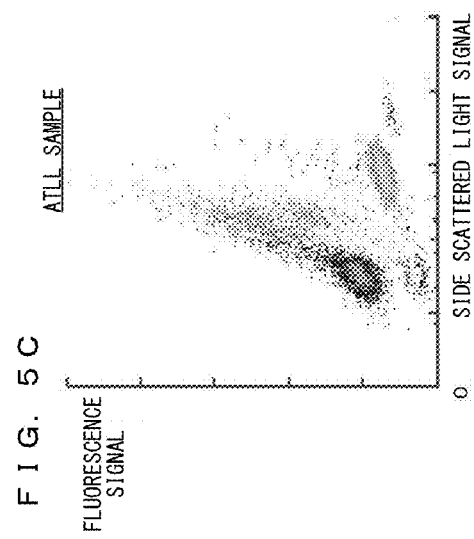

FIG. 5C shows a first scattergram created based on a blood sample collected from a patient having adult T-cell leukemia-lymphoma (ATLL). Also in this case as in the case of a normal sample described above, each blood cell is classified to any of the four subclasses of white blood cell. However, the blood sample of the patient having adult T-cell leukemia-lymphoma (ATLL) may include neoplastic lymphocytes. In such a case, dots corresponding to neoplastic lymphocytes appear in the region shown by a dashed line in FIG. 5B, and are included in the cluster A11 or the cluster A12 as dots corresponding to normal lymphocytes or monocytes. Thus, neoplastic lymphocytes alone cannot be separately detected. Moreover, neither normal lymphocytes alone can be separated, nor monocytes alone can be separated.

Therefore, the inventors of the present application conceived an idea of not plotting dots corresponding to blood cells in two-dimensional space defined by axes of side scattered light signal and fluorescence signal as described above, but of plotting them in three-dimensional space defined by axes of forward scattered light signal, side scattered light signal, and fluorescence signal. Then, as a result of examining data based on a clinical sample, the inventors of the present application found that, in three-dimensional space defined by axes of the above three types of signals, the position of neoplastic lymphocytes are distanced from those of other blood cells. In this manner, the inventors of the present application was successful in accurately isolating neoplastic lymphocytes, by separating blood cells in the three-dimensional space, based on the fact that the positions of neoplastic lymphocytes are distanced from those of other blood cells in the three-dimensional space above. Hereinafter, a technique of isolating neoplastic lymphocytes and separating blood cells into the four subclasses of white blood cell by use of a three-dimensional distribution chart defined by axes of the three types of signals above will be described.

FIG. 6A is a flow chart showing processes performed by the measurement unit 2 and the information processing unit 4.

First, in order to hemolyze red blood cells contained in a blood sample and to fluorescently stain nucleic acid in white blood cells contained in the blood sample, the measurement unit 2 performs a process of preparing a measurement specimen (S1). Specifically, as described above, a blood sample, the first reagent, and the second reagent are mixed together and this mixture solution is heated by the heater H, whereby a measurement specimen is prepared. Subsequently, the measurement unit 2 performs a process of detecting blood cells based on the measurement specimen (S2). Specifically, as described above, the optical detector D obtains a forward scattered light signal, a side scattered light signal, and a fluorescence signal regarding each blood cell. Signals obtained by the measurement unit 2 are transmitted to the information processing unit 4 (S3).

Next, as described above, the CPU 401 of the information processing unit 4 receives the forward scattered light signal, the side scattered light signal, and the fluorescence signal regarding each blood cell from the measurement unit 2 (S11), and stores the received signals in the hard disk 404. Subsequently, the CPU 401 creates a first scattergram based on the received signals, and performs a first demarcation process on the created first scattergram (S12). The first demarcation process is performed according to the technique described with reference to FIGS. 5A to C.

Subsequently, the CPU 401 sets the value of a determination flag stored in the RAM 403 or the hard disk 404 to 0 (S13). Then, the CPU 401 determines whether re-demarcation is necessary, by determining whether the cluster A11 of lymphocytes and the cluster A12 of monocytes, which each have been created in the first demarcation process, are close to each other (S14).

FIG. 6B shows an example of a part where the clusters A11 and A12 are close to each other on the first scattergram. It should be noted that round dots on the left represent dots included in the cluster A11, that is, dots classified as lymphocytes in the first demarcation process, and rectangular dots on the right represent dots included in the cluster A12, that is, dots classified as monocytes in the first demarcation process.

In the above determination of closeness, first, with respect to each of all dots classified as lymphocytes (all dots in the cluster A11), it is determined whether the dot is adjacent to a dot classified as a monocyte. For example, a dot P11 classified as a lymphocyte is adjacent to a dot P21 classified as a monocyte, whereas a dot P12 classified as a lymphocyte is adjacent to none of dots classified as monocytes. In this manner, with respect to each of all dots classified as lymphocytes, it is determined whether the dot is adjacent to a dot classified as a monocyte, and based on the number of dots each determined as being adjacent to a dot classified as a monocyte, whether the clusters A11 and A12 are close to each other is determined.

With reference back to FIG. 6A, in a case where the clusters A11 and A12 are not close to each other, as in FIGS. 5A and 5B, for example, the CPU 401 determine as NO in S14, that is, determines that this blood sample is normal. Then, the CPU 401 counts the number of dots included in each of the clusters A11 to A14 (the number of blood cells belonging to each cluster) (S15). As a result, the numbers of lymphocytes, monocytes, blood cells in the blood cell group including neutrophils and basophils, and eosinophils are obtained.

On the other hand, in a case where the clusters A11 and A12 are close to each other, as in FIG. 5C, for example, the CPU 401 determines as YES in S14, that is, determines that this blood sample has a possibility of including neoplastic lymphocytes. In this case, the CPU 401 sets the value of the determination flag to 1 (S16). Then, based on the signals received in S11, the CPU 401 creates a three-dimensional distribution chart (hereinafter, referred to as "three-dimensional scattergram" defined by axes of forward scattered light signal, side scattered light signal, and fluorescence signal, and performs a second demarcation process on the created three-dimensional scattergram (S17).

Figure 7B:
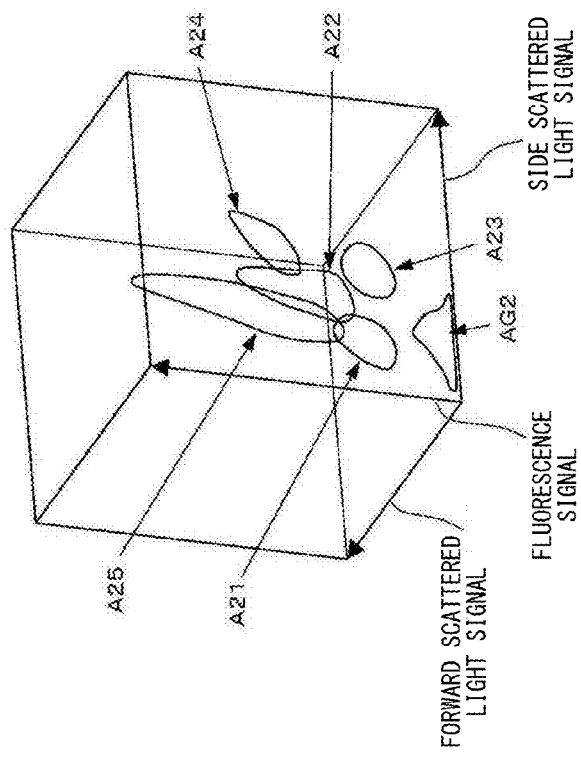
FIGS. 7A to 7C show a three-dimensional scattergram and illustrates a second demarcation process according to an embodiment.
Figure 7C:
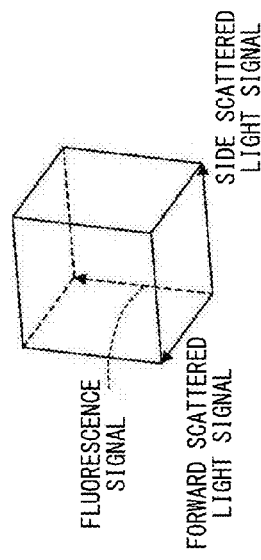
Figure 7A:
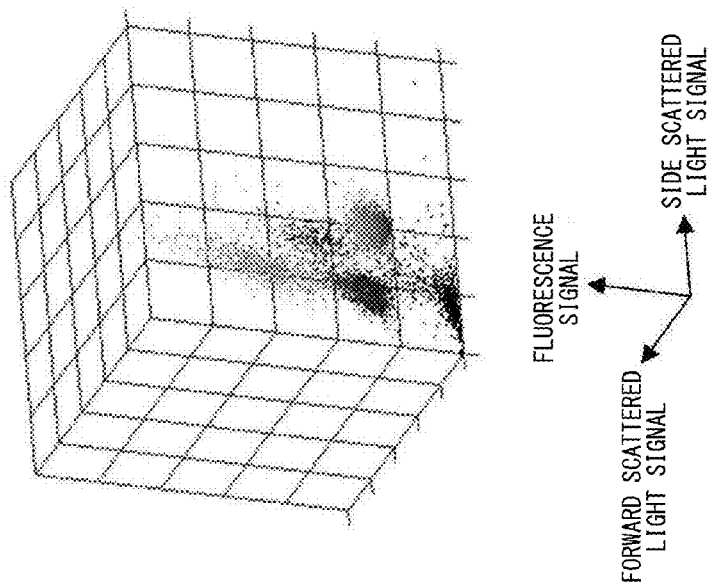

FIG. 7A shows a three-dimensional scattergram and FIG. 7B illustrates the second demarcation process.

With reference to FIG. 7A, based on a forward scattered light signal, a side scattered light signal, and a fluorescence signal regarding each individual blood cell, a three-dimensional scattergram is created by plotting a dot corresponding to each individual blood cell onto a position on a three-dimensional distribution chart that corresponds to the signals. It should be noted that the three axes shown in FIG. 7A are set as shown in FIG. 7C. FIG. 7A shows the inside of FIG. 7C, without the three planes indicated by solid lines in FIG. 7C.

Next, from the dots plotted on the three-dimensional scattergram, dots corresponding to red blood cell ghosts being hemolyzed red blood cells and the like are excluded, as in the first demarcation process above. Specifically, dots included in a predetermined region AG2 set in advance as shown in the schematic diagram in FIG. 7B are excluded. It should be noted that FIG. 7B is a perspective view of the inside of the box of FIG. 7C. Subsequently, each dot on the three-dimensional scattergram from which blood cells in the region AG2 have been excluded is classified into any of four clusters respectively corresponding to the four subclasses of white blood cell (a cluster A21 of lymphocytes, a cluster A22 of monocytes, a cluster A23 of the blood cell group including neutrophils and basophils, and a cluster A24 of eosinophils), and a cluster A25 corresponding to neoplastic lymphocytes.

Specifically, based on the distance between a dot corresponding to each blood cell plotted on the three-dimensional scattergram and the center of gravity of each cluster set in advance, the belonging degree of each blood cell to each cluster is obtained. Here, not only with respect to each of the four clusters respectively corresponding to the four subclasses of white blood cell (the cluster A21 of lymphocytes, the cluster A22 of monocytes, the cluster A23 of the blood cell group including neutrophils and basophils, and the cluster A24 of eosinophils), but also with respect to the cluster A25 corresponding to neoplastic lymphocytes, the center of gravity is set in advance on the three-dimensional space. Then, based on the distance between these centers of gravity and a dot corresponding to each blood cell plotted on the three-dimensional scattergram, the belonging degree of each blood cell to each cluster is obtained. Calculation of the belonging degree is performed by extensionally applying the technique of calculating a belonging degree on a two-dimensional plane described in Japanese Laid-Open Patent Publication No. H5-149863 (corresponding U.S. Pat. No. US5555196), onto three-dimensional space.

When each blood cell has been classified to any of the four subclasses of white blood cell and neoplastic lymphocyte, dots plotted on the three-dimensional scattergram shown in FIG. 7A are separated into the clusters A21 to A25 shown in FIG. 7B. Further, in FIG. 7B, although there are parts where the clusters A21 to A25 seem to overlap adjacent clusters, they do not actually overlap one another in the three-dimensional space. Further, the clusters A21 to A25 are not close to one another as shown in FIG. 6B in the three-dimensional space.

With reference back to FIG. 6A, when the second demarcation process on the three-dimensional scattergram has been completed, the CPU 401 counts the number of dots included in each of the clusters A21 to A25 (the number of blood cells belonging to each cluster) (S18). Then, the CPU 401 determines whether the number of neoplastic lymphocytes (the number of dots included in the cluster A25) is greater than or equal to a predetermined value (S19). When the number of neoplastic lymphocytes is greater than or equal to the predetermined value (S19: YES), the CPU 401 determines that this blood sample may include neoplastic lymphocytes, and sets the value of the determination flag to 2 (S20). On the other hand, when the number of neoplastic lymphocytes is smaller than the predetermined value (S19: NO), the CPU 401 determines that this blood sample does not include neoplastic lymphocytes, and the processing is advanced to S21. It should be noted that, in S19, it may be determined that the blood sample may include neoplastic lymphocytes when the proportion of neoplastic lymphocytes relative to all blood cells exceeds a predetermined threshold value.

Figure 8:
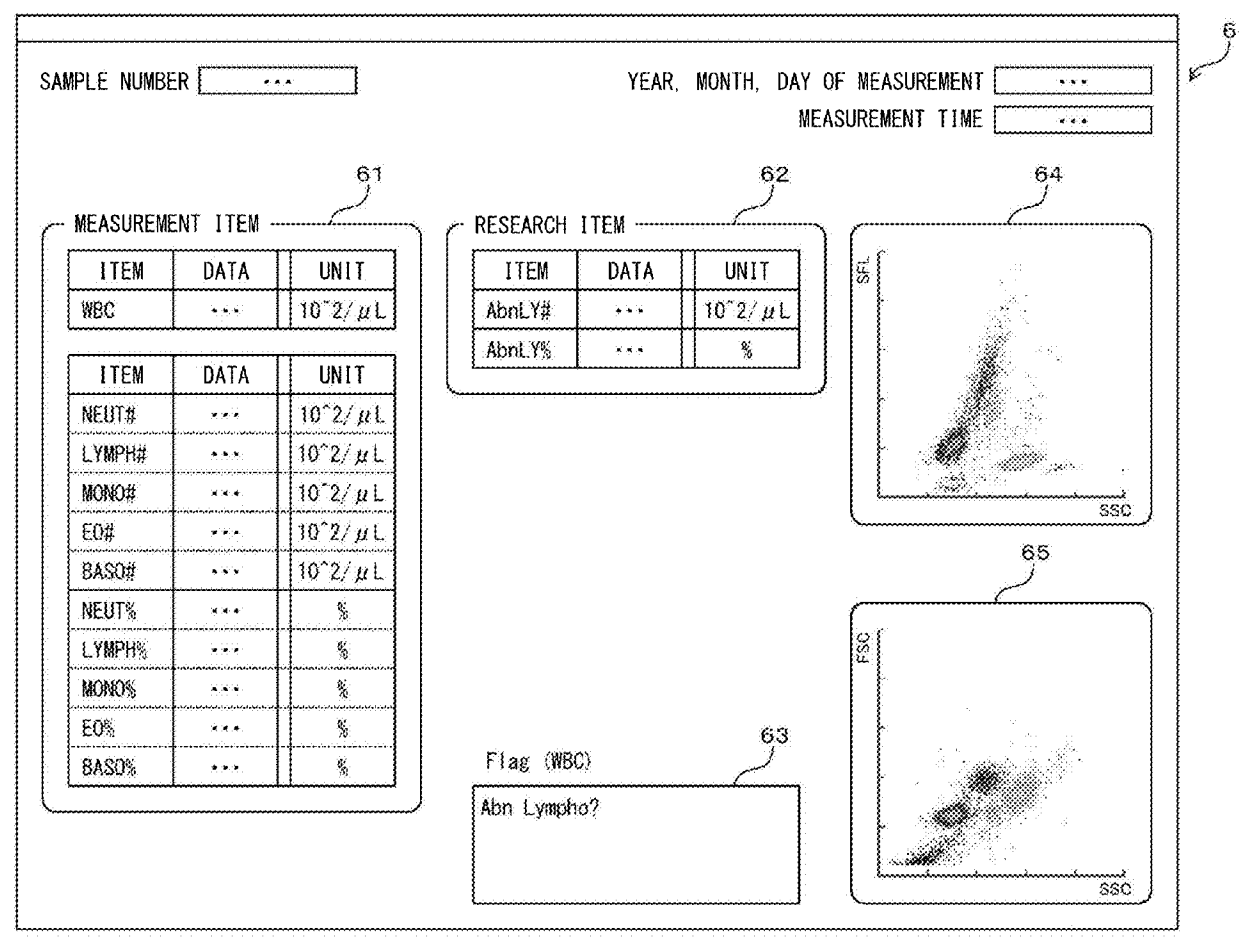
Figure 9:
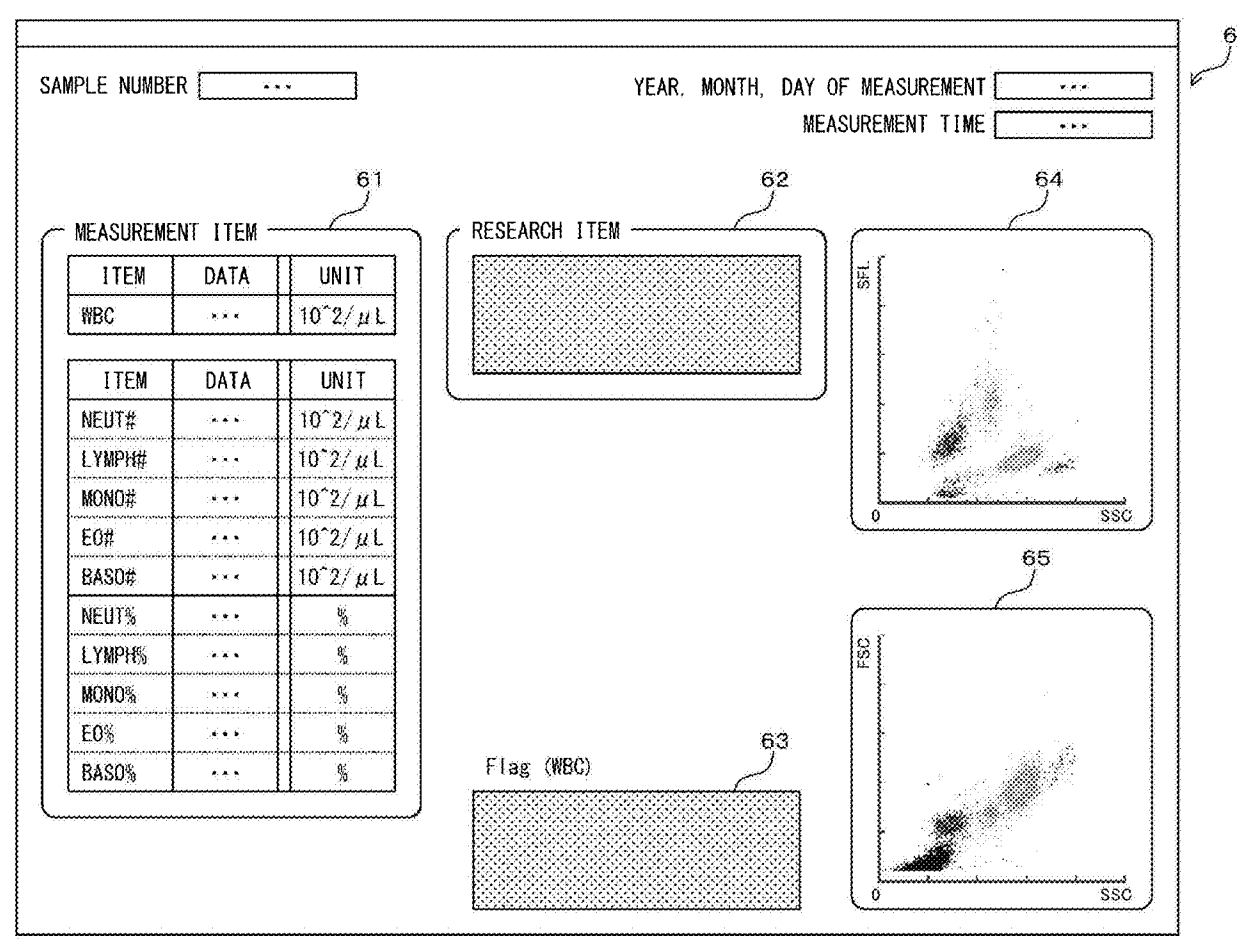

Next, the CPU 401 displays an analysis result screen 6 as shown in FIG. 8 or 9 on the display unit 41 (S21). The analysis result screen 6 includes regions 61 to 65. The region 61 is a region for displaying the number of white blood cells (WBC) and the number of each of neutrophils (NEUT), normal lymphocytes (LYMPH), monocytes (MONO), eosinophils (EO), and basophils (BASO), and their respective proportions relative to the number of white blood cells. The region 62 is a region for displaying the number of neoplastic lymphocytes, and the proportion thereof relative to the number of white blood cells. Then, the CPU 401 displays the analysis result screen 6 in accordance with the value of the determination flag.

In a case where the value of the determination flag is 2 (S22: YES), the CPU 401 displays an alarm indicating that neoplastic lymphocytes may be included, in the region 63 as shown in FIG. 8 (S23). Then, based on the result of the counting performed in S18, the CPU 401 displays measurement results in the regions 61 and 62, and displays first and second scattergrams in the regions 64 and 65, respectively, as shown in FIG. 8 (S24). It should be noted that the second scattergram is created in substantially the same manner as that of the first scattergram. That is, based on a side scattered light signal and a forward scattered light signal regarding each individual blood cell, the second scattergram is created by plotting a dot corresponding to each individual blood cell onto a two-dimensional distribution chart whose horizontal axis represents side scattered light signal and whose vertical axis represents forward scattered light signal.

In a case where the value of the determination flag is 1 (S25: YES), the CPU 401 does not perform display of the region 63 as shown in FIG. 9, but displays measurement results in the regions 61 and 62 based on the result of the counting performed in S18, and displays first and second scattergrams in the regions 64 and 65, respectively, as shown in FIG. 8 (S24). In a case where the value of the determination flag is 0 (S25: NO), the CPU 401 does not perform display of the regions 62 and 63, but displays measurement results in the region 61 based on the result of the counting performed in S12, and displays first and second scattergrams in the regions 64 and 65, respectively, as shown in FIG. 9 (S26).

It should be noted that when displaying the first and second scattergrams in the regions 64 and 65 in S24, the CPU 401 displays, based on the result of the counting performed in S18, dots in the respective clusters A21 to A25 in colors such that classification of dots included in the respective clusters A21 to A25 can be recognized. Further, when displaying the first and second scattergrams in the regions 64 and 65 in S26, the CPU 401 displays, based on the result of the counting performed in S15, dots in the respective clusters A11 to A14 in colors such that classification of dots included in the respective clusters A11 to A14 can be recognized.

FIGS. 10A, 10C, and 10E each show a first scattergram displayed in the region 64 of the analysis result screen 6, and FIGS. 10B, 10D, and 10F each show a second scattergram displayed in the region 65 of the analysis result screen 6.

FIGS. 10A and 10B are first and second scattergrams, respectively, created based on a normal blood sample. In this case, each dot is classified into any of the clusters A11 to A14 as a result of the first demarcation process in S12 shown in FIG. 6A. The first scattergram is a scattergram in which the clusters A11 to A14 are displayed on a two-dimensional space defined by axes of side scattered light signal (SSC) and fluorescence signal (SFL). The second scattergram is a scattergram in which the clusters A11 to A14 are displayed on two-dimensional space defined by axes of side scattered light signal (SSC) and forward scattered light signal (FSC).

At this time, dots included in each of the clusters A11 to A14 displayed on the first scattergram shown in FIG. 10A are displayed in a color different from cluster to cluster. For example, dots included in each of the clusters A11 to A14 are displayed in purple, yellow-green, light blue, or brown. Further, dots included in each of the clusters A11 to A14 displayed on the second scattergram shown in FIG. 10B are also displayed in the same color as that of dots included in a corresponding one of the clusters A11 to A14 shown in FIG. 10A.

FIGS. 10C and 10D are first and second scattergrams, respectively, created based on a blood sample from a patient having an adult T-cell leukemia-lymphoma (ATLL). In this case, each dot is classified into any of the clusters A21 to A25 as a result of the second demarcation process in S17 shown in FIG. 6A. The first scattergram is a scattergram in which the clusters A21 to A25 are displayed on two-dimensional space defined by axes of side scattered light signal (SSC) and fluorescence signal (SFL), and the second scattergram is a scattergram in which the clusters A21 to A25 are displayed on two-dimensional space defined by axes of side scattered light signal (SSC) and forward scattered light signal (FSC).

At this time, dots included in each of the clusters A21 to A25 displayed on the first scattergram shown in FIG. 10C are displayed in a color different from cluster to cluster. For example, dots included in each of the clusters A21 to A25 are displayed in purple, yellow-green, light blue, brown, or red. Further, dots included in each of the clusters A21 to A25 displayed on the second scattergram shown in FIG. 10D are also displayed in the same color as that of dots included in a corresponding one of the clusters A21 to A25 shown in FIG. 10C.

As described above, in a case where neoplastic lymphocytes are included in a blood sample, in the three-dimensional scattergram, dots corresponding to blood cells are separated into the clusters A21 to A25 shown in FIG. 7B. In this case, with reference to the first scattergram shown in FIG. 10C, the user cannot view the clusters A21 to A25, which are separated in five groups on the three-dimensional scattergram, in a state where the clusters A21 to A25 are isolated from one another. However, with reference to the second scattergram shown in FIG. 10D, the user can view the clusters A21 to A25, which are separated into five groups on the three-dimensional scattergram, in a state where the clusters A21 to A25 are isolated from one another.

FIGS. 10E and 10F are first and second scattergrams, respectively, created based on a blood sample of a patient having diffuse large B-cell lymphoma (DLBCL). Also in this case, each dot is classified into any of the clusters A21 to A25 as a result of the second demarcation process. At this time, dots included in each of the clusters A21 to A25 displayed on the first scattergram shown in FIG. 10E are displayed in a color different from cluster to cluster. Dots included in each of the clusters A21 to A25 displayed on the second scattergram shown in FIG. 10F are also displayed in the same color as that of dots included in a corresponding one of the clusters A21 to A25 shown in FIG. 10E.

Also in this case, with reference to the first scattergram shown in FIG. 10E, the user cannot view the clusters A21 to A25, which are separated in five groups on the three-dimensional scattergram, in a state where the clusters A21 to A25 are isolated from one another. However, with reference to the second scattergram shown in FIG. 10F, the user can view the clusters A21 to A25, which are separated in five groups on the three-dimensional scattergram, in a state where the clusters A21 to A25 are isolated from one another.

As described above, according to the present embodiment, in such a case where the clusters A11 and A12 are close to each other (S14: YES), dots on the three-dimensional scattergram shown in FIG. 7A are separated into the clusters A21 to A25 as shown in FIG. 7B. Accordingly, neoplastic lymphocytes contained in a blood sample can be differentiated from other blood cells to be detected. Accordingly, accuracy of classifying normal white blood cells (lymphocytes, monocytes, the blood cell group including neutrophils and basophils, and eosinophils) can be increased, and diagnosis of disease based on the classification can be performed more appropriately. Further, information useful for diagnosis of diseases such as chronic lymphocytic leukemia, malignant lymphoma, and the like can be provided to the user.

According to the present embodiment, necessity/unnecessity of re-demarcation, that is, whether there is a possibility of neoplastic lymphocytes being included, is determined based on the first demarcation process (S14). When re-demarcation is necessary (S14: YES), the second demarcation process is performed on a three-dimensional scattergram (S17). Accordingly, when there is no possibility of neoplastic lymphocytes being included, the second demarcation process, which is three-dimensional analysis, is not performed. Thus, burden of processing for classifying white blood cells can be reduced.

According to the present embodiment, neoplastic lymphocytes contained in a blood sample are detected, differentiated from other blood cells, and blood cells contained in the blood sample can be classified into the four subclasses of white blood cell. The detection and classification in this case can be performed by using only a measurement specimen prepared by mixing a blood sample with the first reagent and the second reagent. That is, without separately preparing a measurement specimen in order to detect neoplastic lymphocytes, the above detection and classification can be performed by use of the measurement specimen prepared for classifying white blood cells.

According to the present embodiment, in a case where neoplastic lymphocytes are contained (see FIG. 5C), neoplastic lymphocytes may be classified as normal lymphocytes in the first demarcation process in S12 as shown in FIG. 5B. However, in the second demarcation process in S17, neoplastic lymphocytes are classified separately from normal lymphocytes. Therefore, normal lymphocytes can be classified appropriately, and accuracy of classifying white blood cells can be increased.

According to the present embodiment, the first and second scattergrams are displayed on the analysis result screen 6. Accordingly, by referring to the first and second scattergrams, the user can easily understand the distribution state of each classified blood cell, and thus, information useful for diagnosis can be smoothly obtained.

According to the present embodiment, the first scattergram is a two-dimensional distribution chart defined by axes of side scattered light signal and fluorescence signal, and the second scattergram is a two-dimensional distribution chart defined by axes of side scattered light signal and forward scattered light signal. Since combinations of signals that are used are different in this manner, the user can further easily understand the distribution state of white blood cells.

According to the present embodiment, since the vertical axis of the first scattergram is fluorescence signal, distribution of blood cells whose nucleic acid is very active (for example, juvenile blood cells and the like) and which can be detected by use of fluorescence can be displayed. Further, with reference to the second scattergram shown in FIGS. 10D and 10F, the user can view the clusters A21 to A25, which are separated in five groups as shown in FIG. 7B, in a state where the clusters A21 to A25 are isolated from one another.

According to the present embodiment, in the first and second scattergrams displayed on the analysis result screen 6, as described with reference to FIGS. 10A to 10F, each dot corresponding to a blood cell is displayed in a color which differs in accordance with its classification. Accordingly, distribution of blood cells that have been classified can be more easily understood. Further, in this case, since dots corresponding to neoplastic lymphocytes are displayed in a color (red) different from other blood cells, distribution of neoplastic lymphocytes are more easily understood, and diagnosis of disease such as chronic lymphocytic leukemia, malignant lymphoma, and the like can be more easily performed.

It should be noted that since neoplastic lymphocyte also is a type of lymphocyte, dots corresponding to neoplastic lymphocytes may be displayed in the same color as that of dots corresponding to normal lymphocytes. That is, in the second scattergram shown in FIGS. 10D and 10F, dots included in the cluster A25 may be displayed in the same color as that of dots included in the cluster A21.

According to the present embodiment, in S15 and S18, the number of blood cells included in each classification is counted. Further, the number and the proportion of blood cells classified into each of the four subclasses of white blood cell are displayed in the region 61 of the analysis result screen 6, and the number and the proportion of blood cells classified as neoplastic lymphocytes are displayed in the region 62 of the analysis result screen 6. Accordingly, the user can quantitatively understand how much blood cells classified in the four subclasses of white blood cell are contained in the measurement specimen, and how much neoplastic lymphocytes are contained in the measurement specimen.

In the present embodiment, in the region 61, the number and the proportion of normal lymphocytes excluding neoplastic lymphocytes are displayed as the number of lymphocytes. However, the present invention is not limited thereto. Normal lymphocytes and neoplastic lymphocytes are collectively counted as lymphocytes, and in the region 61, the total of the number of neoplastic lymphocytes and the number of normal lymphocytes may be displayed as the number of lymphocytes, and the proportion of this total number relative to all blood cells may be displayed as the proportion of lymphocytes.

According to the present embodiment, in S19, when the number of neoplastic lymphocytes is greater than or equal to a predetermined value, information indicating that the blood sample has a possibility of including neoplastic lymphocytes is displayed in the region 63 of the analysis result screen 6. Accordingly, the user can further easily confirm a possibility of disease based on neoplastic lymphocytes.

An embodiment of the present invention has been described. However, the embodiment of the present invention is not limited thereto.

For example, in the above embodiment, irrespective of the value of the determination flag, the first and second scattergrams are displayed on the analysis result screen 6. However, in accordance with the value of the determination flag, either of the first and second scattergrams may be displayed. Further, in a case where the second demarcation process has been performed on the three-dimensional scattergram, the three-dimensional scattergram may be displayed on the analysis result screen 6. Each dot on the three-dimensional scattergram in this case is displayed in a color corresponding to its classification, as in the case of FIGS. 10C to 10F.

In the above embodiment, when the second demarcation process has been performed on the three-dimensional scattergram (S17), dots included in each of the clusters A21 to A25 are counted (S18), and based on the result of this counting, the number and the proportion of blood cells included in each of the four subclasses of white blood cell, and the number and the proportion of neoplastic lymphocytes are displayed on the analysis result screen 6 (S24). However, instead of this, on the three-dimensional scattergram, only dots included in the cluster A25, which correspond to neoplastic lymphocytes, are extracted and these dots are excluded from the first scattergram, whereby a first scattergram not including neoplastic lymphocytes can be re-configured. In this case, the above first demarcation process may be performed again on this re-configured first scattergram, and dots included in each of the clusters respectively corresponding to the four subclasses of white blood cell may be determined again. Then, dots included in these clusters and dots included in the cluster A25 of the three-dimensional scattergram are counted, and based on the result of this counting, the number and the proportion of each type of blood cells may be displayed on the analysis result screen 6.

In the above embodiment, with reference to the second scattergram, the user can view the clusters A21 to A25, which are separated in five groups on the three-dimensional scattergram, in a state where the clusters A21 to A25 are isolated from one another, as shown in FIGS. 10D and 10F. Therefore, in S17 in FIG. 6A, instead of the second demarcation process performed on the three-dimensional scattergram, a demarcation process on the second scattergram may be performed. It should be noted that, in order to accurately perform classification among the four subclasses of white blood cell and neoplastic lymphocyte, it is preferable to perform the second demarcation process based on the three-dimensional scattergram as in the above embodiment.

In the above embodiment, a measurement specimen is prepared by use of the first reagent for staining nucleic acid and the second reagent for hemolyzing red blood cells and damaging cell membranes of white blood cells to an extent that the fluorescent dye can permeate therethrough. However, the present invention is not limited thereto. The measurement specimen may be prepared by use of one reagent that can stain nucleic acid and that can hemolyze red blood cells and damage cell membranes of white blood cells.

In addition to the above, various modifications of the embodiment of the present invention can be made as appropriate without departing from the scope of the technical idea defined by the claims.

What is claimed is:
1. A blood cell analyzer comprising:
a mixing chamber that mixes a sample and a reagent to prepare a measurement specimen for classifying white blood cells, wherein the reagent hemolyzes red blood cells contained in the sample and fluorescently stains nucleic acid in white blood cells contained in the sample;

a piercer that aspirates the sample from a sample container and discharges the aspirated sample into the mixing chamber;

a flow cell;

a laser that emits light to the measurement specimen flowing through the flow cell;

a fluorescence light detector that detects fluorescence light emitted from each blood cell in the measurement specimen;

first and second scattered light detectors that detect side scattered light and forward scattered light from each blood cell in the measurement specimen;

a processor; and a non-transitory computer-readable recording medium storing computer instructions that, when executed by the processor, cause the processor to:

receive, from the fluorescence light detector and the first and second scattered light detectors, a set of intensity signals representing an intensity of the detected fluorescence light and intensities of the side scattered light and the forward scattered light for each blood cell in the measurement specimen;

position a coordinate of a respective set of the intensity signals in a single 3-D coordinate system having three coordinate dimensions representing the intensities of the fluorescent light and the side scattered light and the forward scattered light, wherein the coordinate of the respective set of the intensity signals is uniquely positioned in the single 3-D coordinate system according to the three intensity signals represented by the coordinate; and analyze spatial relationships among the coordinates of the sets of the intensity signals positioned in the single 3-D coordinate system and classify the coordinates of the sets of the intensity signals into at least four groups of the white blood cells and a group of neoplastic lymphocytes.

2. The blood cell analyzer of claim 1, wherein the computer instructions further cause the processor to:

positions the coordinate of the respective set of intensity signals in a single 2-D coordinate system having two coordinate dimensions representing the intensities of the fluorescent light and one of the side scattered light and the forward of scattered light, wherein the coordinate of the respective set of the intensity signals is uniquely positioned in the single 2-D coordinate system according to two of the three intensity signals represented by the coordinate;

analyze spatial relationships among the coordinates of the sets of the intensity signals positioned in the single 2-D coordinate system and classify the coordinates of the sets of the intensity signals into at least four groups of the white blood cells; and proceed to perform the analysis based on the single 3-D coordinate system if existence of a cluster for the neoplastic lymphocytes is suggested as a result of the analysis based on the single 2-D coordinate system.

3. The blood cell analyzer of claim 1, further comprising a display unit configured to display an analysis result from the analysis based on the single 3-D coordinate system.

4. The blood cell analyzer of claim 3, wherein the analysis result comprises a three-dimensional scattergram having three coordinate dimensions representing the intensities of the fluorescent light and the side scattered light and the forward scattered light.

5. The blood cell analyzer of claim 4, wherein the three-dimensional scattergram shows the clusters representing the at least four groups of the white blood cells.

6. The blood cell analyzer of claim 5, wherein the display unit is configured to display information indicating that the sample may include the neoplastic lymphocytes when the processor has identified the group of neoplastic lymphocytes based on the single 3-D coordinate system.

7. The blood cell analyzer of claim 3, wherein the analysis result comprises a first white blood cell distribution chart shown in a 2-dimentional plane having two coordinate dimensions representing the intensities of a combination of two of the fluorescent light and the side scattered light and the forward scattered light, and a second white blood cell distribution chart shown in another 2-dimentional place having two coordinate dimensions representing the intensities of a different combination of two of the fluorescent light and the side scattered light and the forward scattered light.

8. The blood cell analyzer of claim 7, wherein
the first white blood cell distribution chart has two coordinate dimensions representing the intensities of the fluorescent light and one of the side scattered light and the forward scattered light, and
the second white blood cell distribution chart has two coordinate dimensions representing the intensities of the side scattered light and the forward scattered light.

9. The blood cell analyzer of claim 7, wherein the display unit is configured to show the clusters representing white blood cells in colors in the first and second white blood cell distribution charts.

10. The blood cell analyzer of claim 9, wherein the display unit is configured to show the cluster representing the group of neoplastic lymphocytes in a color identical to a color in which a cluster representing a group of normal lymphocytes is shown.

11. The blood cell analyzer of claim 9, wherein the display unit is configured to show the cluster representing the group of neoplastic lymphocytes in a color different from colors in which other clusters are shown.

12. The blood cell analyzer of claim 1, wherein
the computer instructions cause the processor to count the coordinates of sets of signals included in a cluster identified to represent the group of neoplastic lymphocytes, and
the display unit is configured to display a count of the sets of signals in the cluster as a number of neoplastic lymphocytes.

13. The blood cell analyzer of claim 12, wherein the display unit is configured to display information indicating that the sample may include the neoplastic lymphocytes, in accordance with the count of the sets of signals forming the cluster representing the neoplastic lymphocytes.

14. The blood cell analyzer of claim 1, further comprising first and second types of condenser lenses configured to condense the side scattered light and the forward scattered light onto the first and second scattered light detectors, respectively.

15. The blood cell analyzer of claim 1, wherein the mixing chamber is connected to a reagent container containing the reagent and mixes the sample and the reagent supplied from the reagent container.

16. The blood cell analyzer of claim 15, further comprising:
a gripper configured to obtain the sample container from a sample rack; and
a transporting section configured to transport the sample container obtained by the gripper to a position at which the piercer aspirates the sample.

17. The blood cell analyzer of claim 1, further comprising a communication interface for transmitting the set of intensity signals, outputted from the fluorescence light detector and the first and second scattered light detectors, to the processor.

18. The blood cell analyzer of claim 1, wherein the single 2-D coordinate system has two coordinate dimensions representing the intensities of the fluorescence light and the side scattered light, the processor counts the coordinates of sets of signals on a border of lymphocytes and monocytes in the single 2-D coordinate system, and proceeds to perform the analysis based on the single 3-D coordinate system if the counted number exceeds a threshold.

* * * * *